US012797611B2

(12) United States Patent
Park

(10) Patent No.: US 12,797,611 B2
(45) Date of Patent: Nov. 17, 2026

(54) DEEP BRAIN STIMULATION TRANSPARENT ELECTRODE ARRAY AND NEURAL SIGNAL DETECTION METHOD USING SAME

(71) Applicant: University of Seoul Industry Cooperation Foundation, Seoul (KR)

(72) Inventor: Dong Wook Park, Seoul (KR)

(73) Assignee: University of Seoul Industry Cooperation Foundation, Seoul (KR)

( * ) Notice: Subject to any disclaimer, the term of this patent is extended or adjusted under 35 U.S.C. 154(b) by 1072 days.

(21) Appl. No.: 17/790,994

(22) PCT Filed: Jan. 9, 2020

(86) PCT No.: PCT/KR2020/000399
§ 371 (c)(1),
(2) Date: Jul. 6, 2022

(87) PCT Pub. No.: WO2021/141163
PCT Pub. Date: Jul. 15, 2021

(65) Prior Publication Data
US 2023/0045240 A1 Feb. 9, 2023

(51) Int. Cl.
*A61N 1/36* (2006.01)
*A61B 5/00* (2006.01)
(Continued)

(52) U.S. Cl.
CPC ................ *A61N 1/36* (2013.01); *A61B 5/291* (2021.01); *A61B 5/369* (2021.01); *A61B 5/6868* (2013.01); *A61N 1/05* (2013.01)

(58) Field of Classification Search
CPC .. A61N 5/0622; A61N 1/0529; A61N 1/0534; A61N 1/04; A61N 1/02;
(Continued)

(56) References Cited

U.S. PATENT DOCUMENTS

2011/0112591 A1* 5/2011 Seymour .................. A61B 5/24 600/377
2011/0125078 A1* 5/2011 Denison ............... A61N 5/0622 604/20
(Continued)

FOREIGN PATENT DOCUMENTS

JP 2014-008282 A 1/2014
KR 10-1304338 B1 9/2013
(Continued)

OTHER PUBLICATIONS

Park, D. et al. "Graphene-based carbon-layered electrode array technology for neural imaging and optogenetic applications", Nature Communications. 2014, vol. 5, No. 1, thesis No. 5258 (inner pp. 1-11). See Results; Discussion; Methods; and Figures 1-6, Oct. 20, 2014.

*Primary Examiner* — Karen E Toth
(74) *Attorney, Agent, or Firm* — Bridgeway IP Law Group, PLLC; Jihun Kim

(57) ABSTRACT

A deep brain stimulation transparent electrode array and a neural signal detection method using the same are proposed. The deep brain stimulation transparent electrode array includes a biocompatible dielectric substrate, a plurality of electrode sites arranged on one side of the substrate, a plurality of electrically conductive contacts arranged on the other side of the substrate, and an interconnector extended from each electrode site so as to be connected to each contact. The deep brain stimulation transparent electrode array is capable of conducting deep brain electrical stimulation and brain wave detection while minimizing image distortion in magnetic resonance imaging, and accuracy of the deep brain electrical stimulation and the brain wave
(Continued)

detection may be increased by enhancing ability to carry electric current and minimizing the image distortion in the magnetic resonance imaging.

6 Claims, 13 Drawing Sheets

(51) Int. Cl.
*A61B 5/291* (2021.01)
*A61B 5/369* (2021.01)
*A61N 1/05* (2006.01)

(58) Field of Classification Search
CPC ....... A61B 5/293; A61B 5/291; A61B 5/6868; A61B 5/263; A61B 5/271; A61B 2562/04
See application file for complete search history.

(56) References Cited

U.S. PATENT DOCUMENTS

| | | | | |
|---|---|---|---|---|
| 2011/0237921 | A1* | 9/2011 | Askin, III | A61B 5/24 607/116 |
| 2015/0099959 | A1* | 4/2015 | Bonmassar | A61B 5/6868 600/377 |
| 2016/0007874 | A1* | 1/2016 | Ma | A61B 5/6868 600/377 |
| 2021/0244304 | A1* | 8/2021 | Park | H01B 13/0036 |

FOREIGN PATENT DOCUMENTS

| | | | |
|---|---|---|---|
| KR | 10-1461525 | B1 | 11/2014 |
| KR | 10-1741189 | B1 | 5/2017 |
| KR | 10-2020-0016102 | A | 2/2020 |
| KR | 10-2020-0016103 | A | 2/2020 |

* cited by examiner

DEEP BRAIN STIMULATION TRANSPARENT ELECTRODE ARRAY AND NEURAL SIGNAL DETECTION METHOD USING SAME

TECHNICAL FIELD

The present disclosure relates to a deep brain stimulation transparent electrode array and a neural signal detection method using the same, wherein the deep brain stimulation transparent electrode array is capable of conducting deep brain electrical stimulation and brain wave detection while minimizing image distortion in magnetic resonance imaging, and the accuracy of the deep brain electrical stimulation and the brain wave detection is increased by enhancing ability to carry electric current and minimizing the image distortion in the magnetic resonance imaging.

BACKGROUND ART

Therapy using brain electrical stimulation is being widely applied to treatment of neurological diseases such as Parkinson's disease, epilepsy, and Tourette syndrome (i.e. tic disorder). In particular, deep brain stimulation (DBS), which relieves symptoms of the neurological diseases by stimulating the deep brain, is becoming an effective surgical treatment for patients who have difficulty relieving the symptoms with drug therapy. Hundreds of deep brain stimulation procedures are conducted annually at about 20 medical centers in South Korea, and the use of the deep brain stimulation procedures is increasing worldwide.

A deep brain stimulation electrode (hereinafter referred to as DBS electrode) is one of various types of neural electrodes. The deep brain stimulation helps activate dopaminergic neurons by injecting the DBS electrode into the deep brain and applying periodic electrical stimulation. The field of application of such electrical stimulation is expanding to not only Parkinson's disease, essential tremor, depression, epilepsy, but also Alzheimer's, obesity, and addiction treatment. Recently, more active research is being conducted.

However, the conventional DBS electrode is made of opaque metals such as tungsten and platinum, which cause image artifacts in medical images of magnetic resonance imaging (MRI) and the like. Distorted image information may interfere with accurate positioning of the DBS electrode during surgery, or interfere with accurate diagnosis of other neurological diseases after electrode implantation.

The phenomenon of image distortion in MRI occurs because the magnetic susceptibility of metal materials is significantly greater than that of biological tissue and in vivo moisture ($H_2O$). Accordingly, an electrode using a carbon fiber having a relatively small magnetic susceptibility has also been proposed. However, due to a large number of carbon atoms present in a carbon fiber, there is a limit to reduction of the MRI image distortion phenomenon in MRI. In addition, since the carbon fiber has a weak mechanical strength, there is a potential risk that electrical connections may be broken when the carbon fiber is implanted for a long time in vivo.

DISCLOSURE

Technical Problem

An objective of the present disclosure is to provide a deep brain stimulation transparent electrode array capable of conducting deep brain electrical stimulation and brain wave detection while minimizing image distortion in magnetic resonance imaging.

Another objective of the present disclosure is to provide a deep brain stimulation transparent electrode array capable of conducting accurate deep brain electrical stimulation and brain wave detection by enhancing ability to carry electric current in vivo and minimizing image distortion in magnetic resonance imaging.

Yet another objective of the present disclosure is to provide a neural signal detection method by using a deep brain stimulation transparent electrode array.

Technical Solution

According to an exemplary embodiment of the present disclosure, there is provided a deep brain stimulation transparent electrode array including: a biocompatible dielectric substrate; a plurality of electrode sites arranged on one side of the substrate; a plurality of electrically conductive contacts arranged on the other side of the substrate; and an interconnector extended from each electrode site so as to be connected to each contact, wherein each electrode site is made of a metal material, and the interconnector is made of a carbon material.

The metal material may be any one selected from a group consisting of platinum, iridium, tungsten, iron, nickel, copper, zinc, titanium, aluminum, silver, gold, and alloys thereof.

The carbon material may be any one selected from a group consisting of graphene, carbon nanotubes, carbon nanofibers, fullerene, and expanded graphite.

The carbon material may be in a form of one to ten layers of graphene sheets.

Respective junction parts between the electrode sites and the interconnector may be subjected to thermal annealing or current annealing.

The deep brain stimulation transparent electrode array may further include an optical fiber bonded to a lower side of the substrate.

According to another exemplary embodiment of the present disclosure, there is provided a deep brain stimulation transparent electrode array including: a biocompatible dielectric substrate; a plurality of electrode sites arranged on one side of the substrate and comprising respective graphene sheets; a plurality of electrically conductive contacts arranged on the other side of the substrate; an electrically conductive interconnector configured to connect the electrode sites and the contacts to each other; and an optical fiber bonded to a lower side of the substrate.

The substrate may be arranged to surround the optical fiber.

The substrate and the optical fiber may be bonded to each other by any one adhesive selected from a group consisting of polydimethylsiloxane, polyimide, and silylated polyurethanes.

A length of one end of the substrate may be longer than a length of one end of the optical fiber, and the one end of the substrate may be folded toward the one end of the optical fiber, so that a part or all of each electrode site covers the one end of the optical fiber.

According to yet another exemplary embodiment of the present disclosure, there is provided a method of detecting neural signals using a deep brain stimulation transparent electrode array.

The method of detecting the neural signals may include: inserting the deep brain stimulation transparent electrode array onto electrically active biological tissue; and recording a neural response generated by nerve cells in the nerve tissue at each electrode site.

Advantageous Effects

The deep brain stimulation transparent electrode array of the present disclosure is capable of conducting the deep brain electrical stimulation and the brain wave detection while minimizing image distortion in magnetic resonance imaging.

In addition, the deep brain stimulation transparent electrode array of the present disclosure may be used to perform fusion studies on nerve cell stimulation through light stimulation.

In addition, the deep brain stimulation transparent electrode array of the present disclosure may increase the accuracy of deep brain electrical stimulation and brain wave detection by enhancing the ability to carry electric current in vivo and minimizing the image distortion in magnetic resonance imaging.

In addition, the deep brain stimulation transparent electrode array of the present disclosure may observe, outside a living body, optical signals generated inside the living body.

BEST MODE

Figure 1:
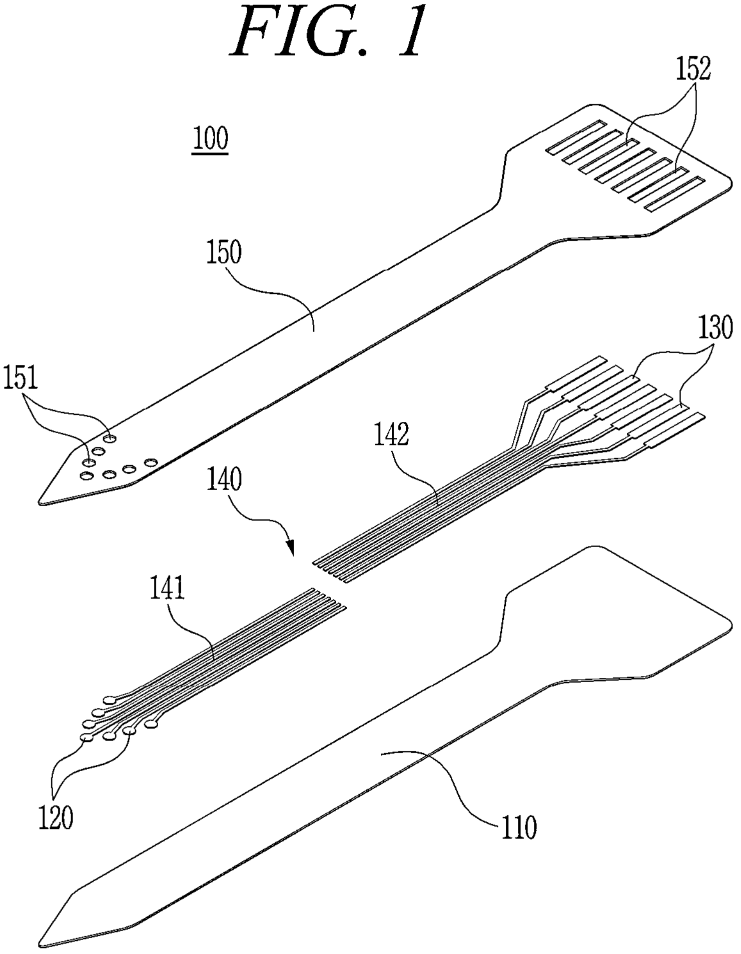
FIG. 1 is a view illustrating a deep brain stimulation transparent electrode array according to an exemplary embodiment of the present disclosure.

Hereinafter, exemplary embodiments of the present disclosure will be described in detail with reference to the accompanying drawings so that those skilled in the art can easily implement the present disclosure. However, the present disclosure is not limited to the exemplary embodiments described herein and may be embodied in many different forms. Throughout the specification, like reference numerals are assigned to similar parts.

FIG. 1 is a view illustrating a deep brain stimulation transparent electrode array 100 according to an exemplary embodiment of the present disclosure. A transparent graphene neural electrode includes: a biocompatible dielectric substrate 110; a plurality of electrode sites 120 arranged on one side of the substrate; a plurality of electrically conductive contacts 130 arranged on the other side of the substrate; and an electrically conductive interconnector 140 configured to connect the electrode sites 120 and the contacts 130 to each other.

The interconnector 140 refers to a component consisting of circuits 141 configured to transmit respective electrical signals of the electrode sites 120, circuits 142 configured to transmit respective electrical signals of the contacts 130, and connecting parts with which the circuits are in contact.

Figure 2:
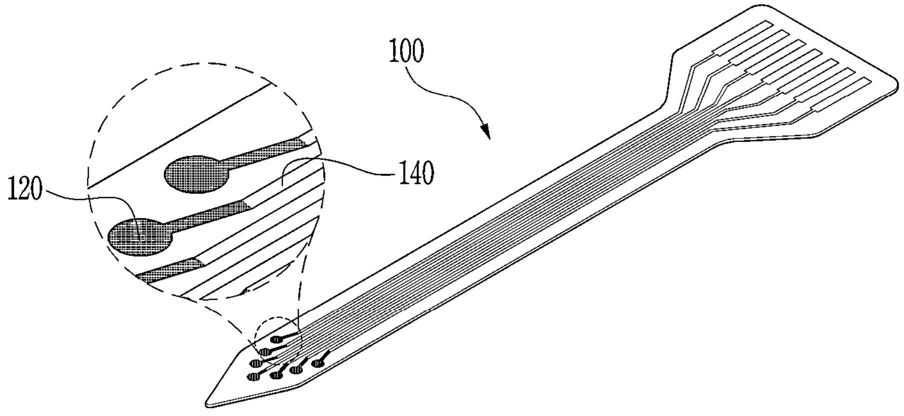
FIG. 2 is a view illustrating electrode sites and an interconnector of the deep brain stimulation transparent electrode array.

The deep brain stimulation transparent electrode array 100 is characterized in that each electrode site 120 is made of a metal material, and the interconnector 140 is a hybrid electrode made of a carbon material. The connecting parts between the electrode sites 120 and the interconnector 140 are shown in FIG. 2.

The metal material may be any one selected from a group consisting of platinum, iridium, tungsten, iron, nickel, copper, zinc, titanium, aluminum, silver, gold, and alloys thereof. The metal material may be a pure metal or an alloy, and may be an oxide of a metal. As a material, various forms are possible, such as a metal plate, a multilayer metal film, a spherical metal particle, a metal mesh, a metal gauze, a perforated metal foil, a sintered metal fiber mesh, etc. The present disclosure is not limited by a geometric structure and elemental composition of the material.

Specifically, each electrode site 120 part for the purpose of carrying electric current in a living body or cells is most preferable to be made of platinum or a platinum-iridium alloy having a low impedance and a large current tolerance.

Fine image distortion, which may occur when the metal part of each electrode site 120 is made of platinum or a platinum-iridium alloy, may serve to guide an electrode at a correct position during in vivo injection.

Meanwhile, the electrically conductive contacts 130 positioned on the opposite side of the electrode sites may also be made of a metal material, and it is most preferable to use tungsten, which has relatively little distortion in magnetic resonance imaging.

The interconnector 140 may be made of a carbon material having a low magnetic susceptibility, and the carbon material may be any one selected from a group consisting of graphene, carbon nanotubes, carbon nanofibers, fullerene, and expanded graphite.

The interconnector 140 serves to connect the electrode sites 120 and the electrically conductive contacts 130 to each other in the deep brain stimulation transparent electrode array 100, and occupies a large portion of the entire electrode, so improving the transparency of the interconnector 140 is effective in reducing image distortion.

Specifically, the material of the interconnector 140 is most preferable to be graphene, and the graphene may be included in a form of a single graphene sheet, or two or more graphene sheets. The graphene sheets may provide high electrical conductivity as the number of sheets thereof increases, but since transparency may be reduced, it is most preferable that the number of layers of the graphene sheets present in the interconnector 140 part is one to ten.

The graphene sheet has wavelengths in the ultraviolet (UV), visible (vis), and infrared (IR) regions of the electromagnetic spectrum, and may be transparent in a wide wavelength range, and specifically, may be transparent in a wavelength range of 300 nm to 2000 nm.

A graphene electrode using the carbon material allows a current of about 100 to 200 μA to flow, and when a current of more than the allowed current flows, the impedance increases, whereby the performance tends to decrease after the current is applied. Whereas, the metal material may allow a current of 500 μA or more to flow, so there is an advantage in that the amount of current (i.e. charge amount) that may be transmitted through the metal material is high.

Meanwhile, as for a carbon material, there is an advantage in that the carbon material has low magnetic susceptibility and may exhibit transparent characteristics in a certain wavelength range.

The deep brain stimulation transparent electrode array 100 according to the present disclosure is a hybrid electrode, which includes the electrode sites 120 made of the metal material having a high amount of current (i.e. charge amount) and the interconnector 140 made of the carbon material having high transparency, and has advantages both in terms of image distortion prevention and current transfer.

In order to reduce contact resistance of junction parts between the electrode sites 120 made of the metal material and the interconnector 140 made of the carbon material, thermal annealing or current annealing may be performed on the parts where the metal material and the carbon material are in contact with each other. The annealing is not limited as long as the annealing is a method of changing characteristics by rapidly changing respective temperatures of the surfaces of the metal material and the carbon material. However, specifically, impurities are removed by nitric acid treatment of the metal material and the carbon material, and then in order to prevent nucleation of the carbon material, copper foil from which impurities have been removed is annealed at 200 to 400° C. while supplying $H_2$ gas under Ar atmosphere and a pressure of 90 to 110 torr. Thereafter, in the annealing, oxidation treatment may be performed at 150 to 300° C. for five to seven hours. Since the biocompatible dielectric substrate 110 used in the present disclosure is weak to heat, it is most preferable to conduct the annealing at the temperature within 200 to 400° C.

The deep brain stimulation transparent electrode array 100 may further include an overlayer 150 on the electrode sites 120 and the contacts 130. The overlayer 150 protects and isolates the interconnector 140. The overlayer 150 may be provided with openings 151 and 152 so that the electrode sites 120 and the contacts 130 are exposed and connected to an external device.

The contacts 130 receive signals recorded at the electrode sites 120, amplify, display, store, analyze, and allow the electrode sites 120 to be electrically connected to the external device.

The substrate 110 may be formed of a transparent biocompatible dielectric material. In the present disclosure, "biocompatible" means that the material does not harm or irritate scars of neighboring tissue, and does not degrade an intended function in characteristics of a living tissue to be implanted. The substrate 110 may be entirely transparent and made of a biocompatible material, but when necessary, the substrate 110 may be partially opaque or include a non-biocompatible material.

In addition, the substrate 110 is mechanically flexible so that the substrate 110 may conform to tissue, such as surfaces of the cerebral cortex, without cracking, splitting, or doing other damage to a device.

The overlayer 150, like the substrate 110, may also include a transparent and biocompatible dielectric material and may be mechanically flexible. The overlayer 150 may be made of the same material as that of the substrate 110, but is not limited thereto.

Polymers that may be used as the material of the substrate 110 and the overlayer 150 may be any one selected from a group consisting of parylene C, polyethylene, polydimethylsiloxane (PDMS), polyester (PET), polyimide (PI), polyethylene naphthalate (PEN), polyetherimide (PEI), and copolymers thereof.

In addition, the polymer may be a shape memory polymer, i.e., a polymer that undergoes a planar to non-planar transformation in response to a change in temperature. For example, the shape memory polymer may have a planar structure at room temperature (about 23° C.), but may adopt a non-planar shape at the body temperature of a subject to which the transparent graphene neural electrode 100 is implanted.

Examples of such transparent, biocompatible, and dielectric shape memory polymers are disclosed in T. Ware, D. Simon, R. L. Rennaker, W. Voit, Smart Polymers for Neural Interfaces, Polymer Reviews 53 (1), 108-129, and also in Xie T. Recent Advances in Polymer Shape Memory. Polym. 2011; 52:4985-5000. The content of the examples relates to shape memory polymers and is therefore incorporated herein by reference.

Preferably, each of the substrate 110 and the overlayer 150 have a sufficiently thin thickness in order to provide a sufficiently transparent and mechanically flexible device. Specifically, the thickness of each of the substrate 110 and the overlayer 150 may be 100 μm or less, preferably 50 μm or less, and most preferably, may have a thickness of 20 μm or less.

The transparency of the deep brain stimulation transparent electrode array 100 reflects the combined transparency of the graphene sheet, the substrate 110 material, and the overlayer 150 material. In the exemplary embodiment, the transparency of the deep brain stimulation transparent electrode array has wavelengths in the ultraviolet (UV), visible (vis), and infrared (IR) regions of the electromagnetic spectrum, and may be transparent in a wide wavelength range, and specifically, may be transparent in a wavelength range of 300 nm to 2000 nm, and more preferably, may be transparent in a wavelength range of 400 nm to 1800 nm.

Figure 3:
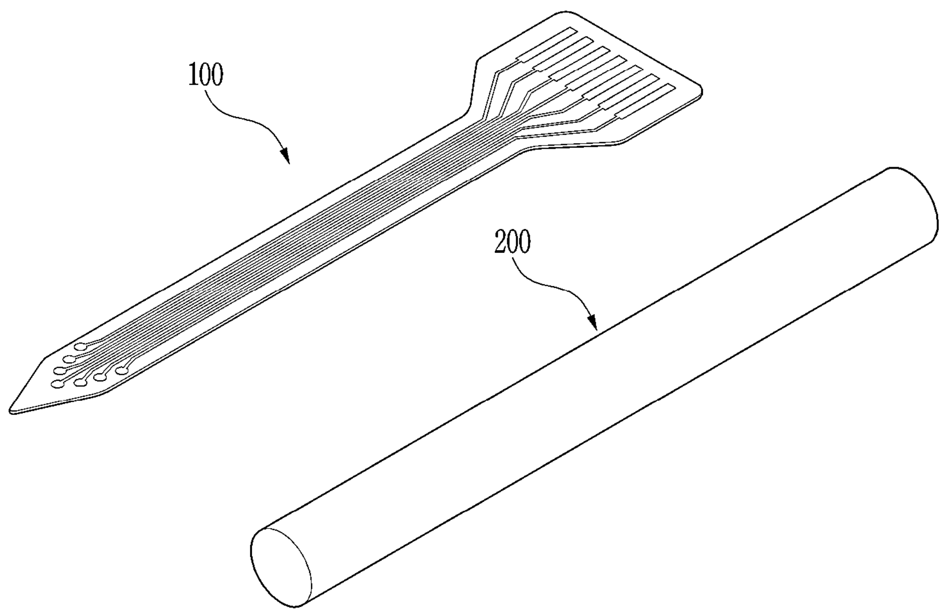
FIG. 3 is an exploded perspective view illustrating the deep brain stimulation transparent electrode array, including an optical fiber.

The deep brain stimulation transparent electrode array 100 may further include an optical fiber 200 bonded to a lower side of the substrate. FIG. 3 is an exploded perspective view illustrating the deep brain stimulation transparent electrode array 100, including the optical fiber 200.

The deep brain stimulation transparent electrode array 100 may further include the optical fiber 200, and thus may detect electrical signals generated in response to optical stimuli.

Specifically, optogenetics is an example of technology that uses light stimulation to induce nerve stimulation. The optogenetics uses modified biological cells in order to introduce light-sensitive proteins, such as channelrhodop sin (ChR) and halorhodop sin (NpHR), into cell membranes. These proteins serves as ion channels activated by light, thereby allowing a flow of specific ions into and out of the cells when exposed to the light having a specific wavelength. Depending on types of the ion channels, ion diffusion leads to depolarization or hyperpolarization of cells, and may cause excitation or inhibition of nerve activity in a case of nerve cells. When photosensitized cells are exposed to incident light of an appropriate wavelength, optically evoked neural signals are generated. Appropriate wavelength ranges are changed depending on particular photosensitive proteins that are being used. However, typically, incident light having a wavelength in the UV or visible light range is used. In the present disclosure, the optical fiber 200 is thus included in order to input such incident light.

Figure 4:
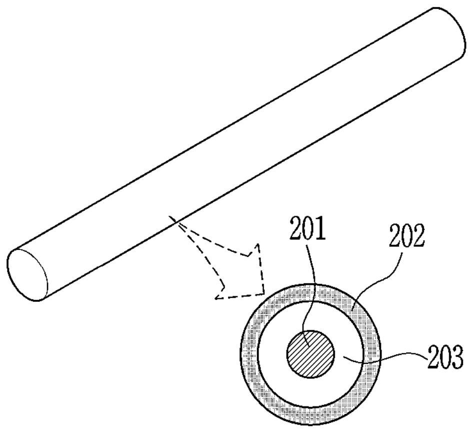
FIG. 4 is a view illustrating the optical fiber.

An example of the optical fiber 200 is shown in FIG. 4. The optical fiber is made of glass or plastic, and may be composed of a core 201 configured to be an area where light actually propagates, and a cladding 203 configured to serve to form a wave guide that surrounds the core and confines the light to the core. However, the present disclosure is not limited thereto, and the optical fiber 200 may also be made by using an optical fiber that is formed of only the core 201 without the cladding 203.

The optical fiber 200 may further include an adhesive layer 202 for adhesion to the deep brain stimulation transparent electrode array 100. In addition, the adhesive layer 202 may serve as a coating to protect the core 201 from physical or environmental damage and to improve strength of the core 201.

The adhesive layer 202 may include any one silicone-based polymer selected from a group consisting of polydimethylsiloxane, polyimide, and silylated polyurethanes. The silicone-based polymer is most preferably polydimethylsiloxane for reasons of high transparency, biocompatibility, and the like.

In addition, the optical fiber 200 may further include: a light emitting part (not shown) for transmitting input optical signals to the optical fiber; and a light receiving part (not shown) for measuring the amount of light of output optical signals passing through the optical fiber. The light emitting part and the light receiving part may be respectively formed on one end and the other end of the optical fiber 200, or the light emitting part and the light receiving part may also be formed together on the one end of the optical fiber 200 by forming a reflective layer on the other end of the optical fiber 200 so that the optical signals may be reflected.

The optical fiber 200 may have a diameter of 50 micrometers (μm) to 1 millimeter (mm). When the diameter is less than 50 μm, there may be reliability problems such as an insertion problem into the brain and the snapping of a wire due to the thin thickness, and when the diameter exceeds 1 mm, there may be problems such as excessive damage to nerve cells.

The optical fiber 200 may be used as a single fiber, or a string of optical fiber bundles.

Meanwhile, in the deep brain stimulation transparent electrode array 100 including the optical fiber, the substrate 110 may be arranged to surround the optical fiber 200. In this case, since the substrate 110 may also serve as the cladding 203 of the optical fiber 200, the optical fiber 200 may be formed of only the core 201 as described above.

Figure 5:
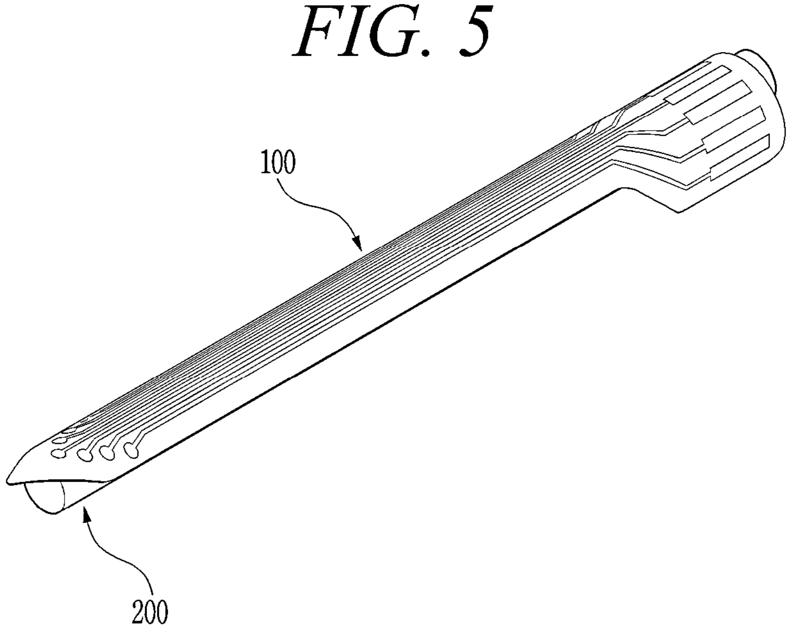
FIG. 5 is a view illustrating an example of the deep brain stimulation transparent electrode array including the optical fiber.
Figure 6:
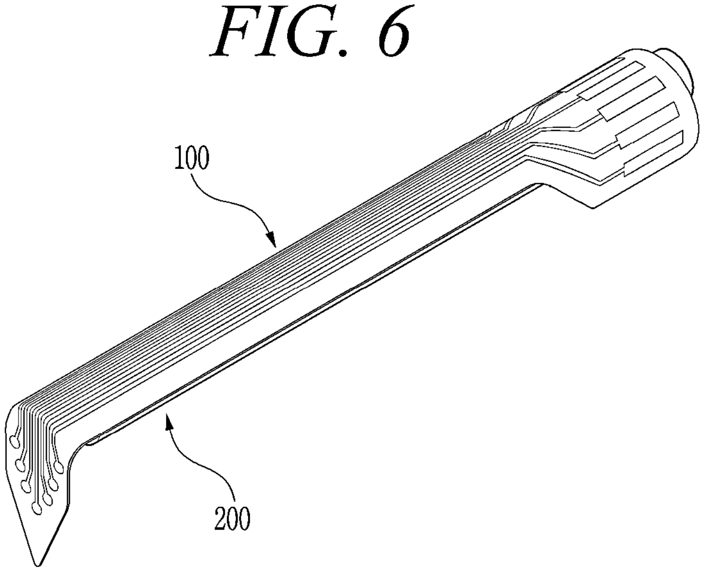
FIG. 6 is a view illustrating another example of the deep brain stimulation transparent electrode array including the optical fiber.

FIGS. 5 and 6 are views illustrating respective cases in which the substrate 110 is arranged to surround the optical fiber 200. In this case, the electrode sites 120 of the deep brain stimulation transparent electrode array 100 may be positioned on a periphery of the optical fiber 200 as shown in FIG. 5, and may be positioned at the end of the optical fiber 200 as shown in FIG. 6.

Describing the electrode sites 120 positioned at an end of the optical fiber 200 in more detail, a length of one end of the deep brain stimulation transparent electrode array 100 is longer than a length of one end of the optical fiber 200, and the one end of the deep brain stimulation transparent electrode array 100 is folded toward the one end of the optical fiber 200, whereby a part or all of the electrode sites 120 of the deep brain stimulation transparent electrode array 100 may cover the one end of the optical fiber 200. In this case, it is possible to obtain an effect where the optical stimulation through an optical fiber, or the electrical signal detection through optical signal extraction sites and a transparent electrode may be conducted in the same nerve cells. That is, the effect of using the transparent electrode may be maximally increased by directly detecting signals from the nerve cells positioned at the end of the transparent electrode and the optical fiber. In this case, in contrast to a case of using an opaque metal electrode instead of the transparent electrode, the effect may be clearly confirmed.

Meanwhile, according to another exemplary embodiment of the present disclosure, when the deep brain stimulation transparent electrode array 100 includes the optical fiber 200, the deep brain stimulation transparent electrode array 100 may include a plurality of electrode sites 120 respectively including graphene sheets 121.

Figure 7:
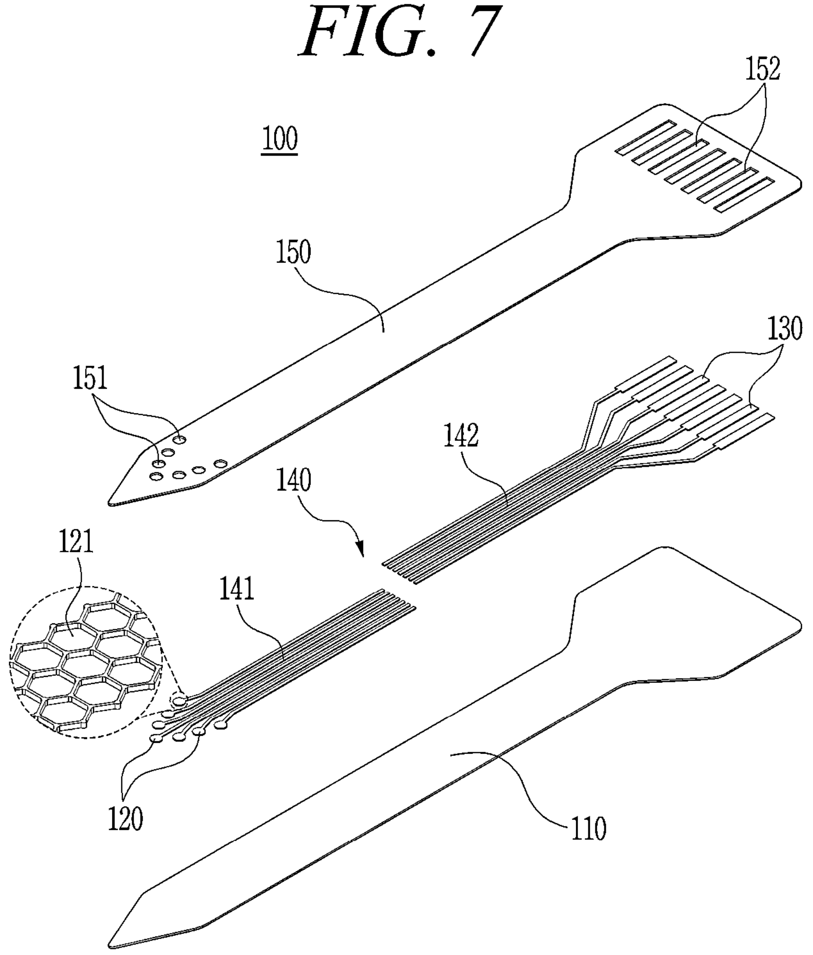
FIG. 7 is a view illustrating a deep brain stimulation transparent electrode array according to another exemplary embodiment of the present disclosure.

FIG. 7 is a view illustrating the deep brain stimulation transparent electrode array 100 including the plurality of electrode sites 120 respectively including the graphene sheets 121. The deep brain stimulation transparent electrode array 100 includes: a biocompatible dielectric substrate 110; a plurality of electrode sites 120 arranged on one side of the substrate and respectively including graphene sheets 121; a plurality of electrically conductive contacts 130 arranged on the other side of the substrate; and an electrically conductive interconnector 140 configured to connect the electrode sites 120 and the contacts 130 to each other.

Each of the electrode sites 120 includes a single layer, or two or more layers of the graphene sheets 121. Each graphene sheet 121 has wavelengths in the ultraviolet (UV), visible (vis), and infrared (IR) regions of the electromagnetic spectrum, and may be transparent in a wide wavelength range, and specifically, may be transparent in a wavelength range of 300 nm to 2000 nm.

The graphene sheets 121 may provide high electrical conductivity as the number of sheets thereof increases, but since the transparency thereof may also be decreased, it is most preferable that the number of layers of the graphene sheets 121 present in each electrode site is one to ten.

Hereinafter, a method of detecting neural signals using the deep brain stimulation transparent electrode array 100 will be described in detail.

Specifically, the method of detecting the neural signals includes: inserting the deep brain stimulation transparent electrode array onto electrically active biological tissue; and recording a neural response generated by nerve cells in the nerve tissue at electrode sites.

In the method of detecting the neural signals by using the deep brain stimulation transparent electrode array, since the deep brain stimulation transparent electrode array exhibits a transparent characteristic, there is an advantage in which the tissue underlying the electrode sites may be imaged even while the deep brain stimulation transparent electrode array is inserted deep into the brain to take electrophysiological recordings. Specifically, an image of tissue is obtained by directing incident light to the tissue, and recording the light reflected from the tissue through the transparent electrode sites and transmitted through the transparent electrode sites, wherein the returned light may be the light reflected by the tissue or the light emitted by the tissue in response to the incident light. Imaging technologies that may be used in conjunction with the electrophysiology include fluorescence microscopy, optical coherence tomography (OCT) technology, magnetic resonance imaging (MRI), computed tomography (CT), etc. In this case, since the deep brain stimulation transparent electrode array is transparent and does not reflect or distort light, the imaging may not be disturbed.

In the fluorescence microscopy, the tissue is labeled with a fluorescent biomarker. This labeling may be achieved, for example, by injecting a fluorescently labeled probe into a blood vessel that penetrates the tissue. Incident light having a wavelength suitable for inducing a fluorescent substance is directed onto the tissue, and as a result, the fluorescence is recorded by a light detector such as a fluorescence microscope. The optimal wavelength for the incident light depends on a particular fluorophore and an excitation process. Typically, incident wavelengths include wavelengths in a range of about 400 nm to about 1800 nm.

In the optical coherence tomography technique, imaging is performed by measuring an echo time delay and an intensity backscattered from the tissue. As such, an optical coherence tomography image shows a difference in optical backscattering in a cross-sectional plane or a tissue volume. The optical coherence tomography imaging is performed by directing a beam of incident light onto the tissue in which a portion of the light is backscattered from a boundary between a structure having different optical characteristics and a different structure.

Typically, the incident light is short-wave light or continuous wave light with short interference length, each having a wavelength in the infrared region of the electromagnetic spectrum having wavelengths in a range of about 700 nm to about 1 mm. The shapes and dimensions of various structures in tissue are determined through echo measurements.

The magnetic resonance imaging uses a magnetic field and an electric field to generate an image of an organ of the body. In the magnetic resonance imaging, an image is generated by distinguishing materials by using the fact that a degree (i.e. magnetic susceptibility) to which each material that makes up the body responds to the magnetic field is different. Carbon that makes up graphene has no significant difference in the magnetic susceptibility to moisture ($H_2O$), hydrogen (H), etc., which make up the body, so carbon appears transparent in MRI images as well. Whereas, most metals having large magnetic susceptibility cause large image distortion in the MRI images.

The computed tomography technique uses a computer-processed combination of X-ray measurements to generate a tomography image in a specific area, thereby enabling a user to view inside a living body. Similar to MRI imaging, the carbon component constituting graphene has a similar response to X-rays to that of the biological components, so image distortion may be minimized unlike metals.

Mode for Invention

Hereinafter, exemplary embodiments of the present disclosure will be described in detail so that those skilled in the art can easily implement the present disclosure. However, the present disclosure is not limited to the exemplary embodiments described herein and may be embodied in many different forms.

PRODUCTION EXAMPLE 1

Producing Deep Brain Stimulation Transparent Electrode Array

Electrode sites according to the following Exemplary Embodiments and Comparative Examples are produced by using the materials of Table 1 below. The deep brain stimulation electrode array of FIG. 7 is produced by using the produced electrode sites. Exemplary Embodiment 1 including an optical fiber is as shown in FIG. 5.

TABLE 1

| | Exemplary Embodiment 1 | Comparative Example 1 | Comparative Example 2 | Comparative Example 3 | Comparative Example 4 |
|---|---|---|---|---|---|
| Electrode site material (thickness) | Graphene | Tungsten (100 μm) | Tungsten (50 μm) | Platinum (100 μm) | Platinum-Iridium (127 μm) |
| Optical fiber | ○ | X | X | X | X |

EXPERIMENTAL EXAMPLE 1

Phantom Brain and Animal Experiments

Figure 8:
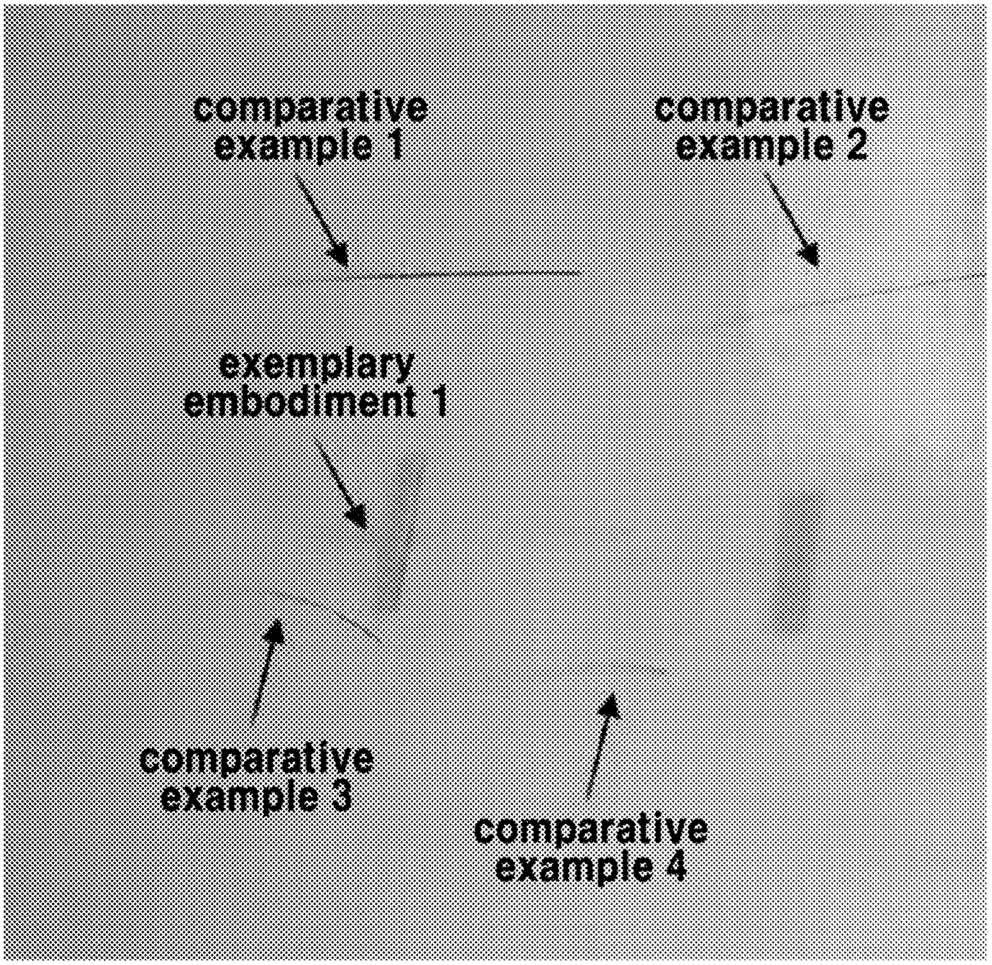
FIGS. 8 and 9 are views respectively illustrating MRI images of an injected nerve electrode according to Experimental Example 1.
Figure 9:
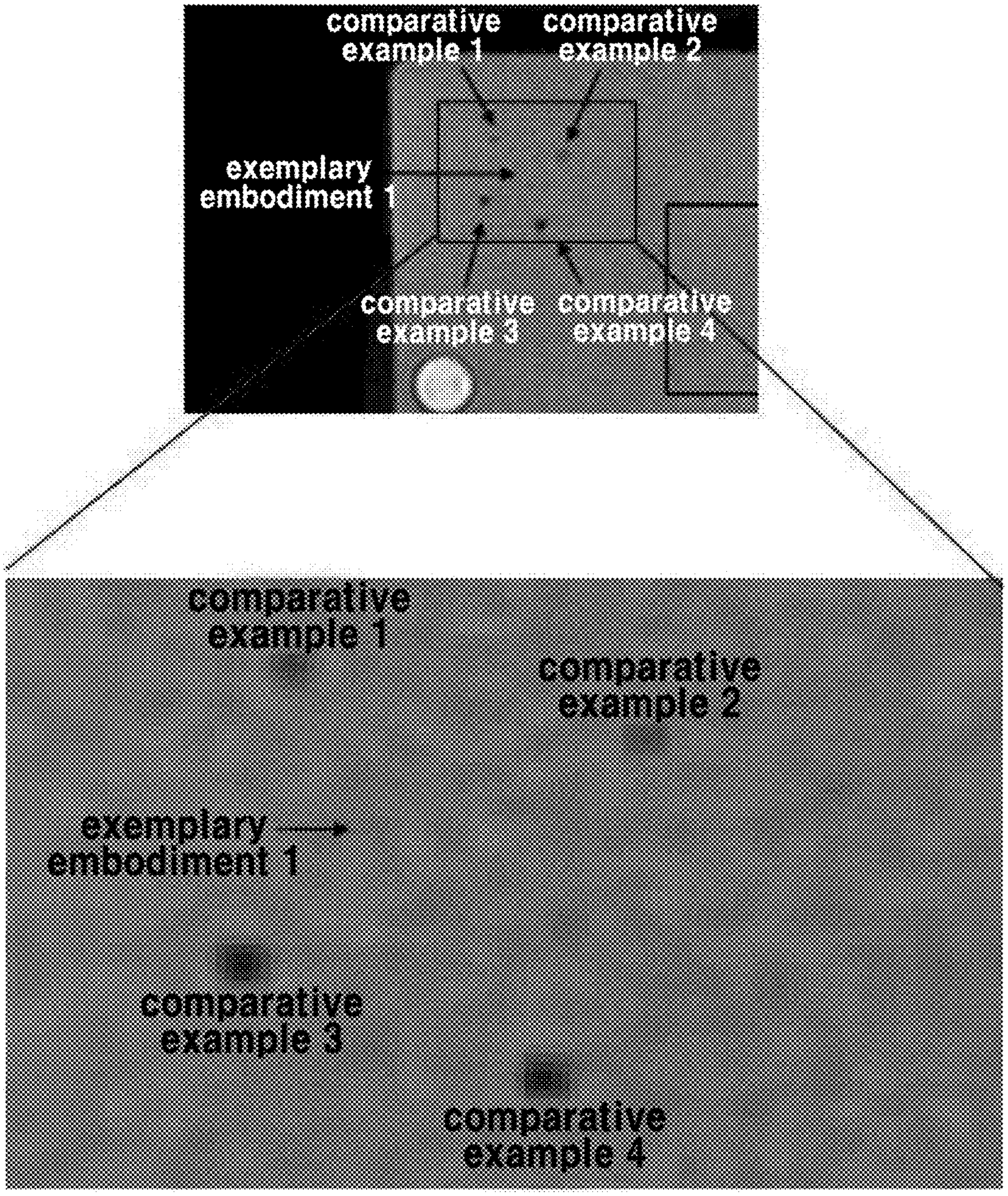

In order to evaluate MRI image distortion caused by an injected nerve electrode, a phantom brain using agarose gel is created and MRI research is conducted. The electrode array produced in Production Example 1 is injected into the phantom brain, so as to compare a difference in degrees of MRI image distortion depending on magnetic susceptibility, whereby results are shown FIGS. 8 and 9.

Referring to the drawings, compared to tungsten (Comparative Examples 1 and 2), platinum (Comparative Example 3), and platinum-iridium (Comparative Example 4), which are commonly used as conventional neural electrodes, it may be confirmed that the combination of graphene and an optical fiber (Exemplary Embodiment 1) has no image distortion to the extent that the image distortion is almost indistinguishable in a 1.5 T MRI image. As a result, it is expected to be helpful for precise medical diagnosis by providing low-distortion medical images, in addition to the optical and electrical signal detection capabilities of the combination of the graphene transparent electrode and the optical fiber.

EXPERIMENTAL EXAMPLE 2

Comparing Impedance of Graphene Electrode Sites and Platinum Electrode Sites After a graphene material and a platinum material are used to produce respective electrode sites, impedance (Ω) and phase (°) measurement results measured in a similar biological environment are compared and respectively shown in FIGS. 10 to 13.

TABLE 2

| | Comparative Example 5 | Exemplary Embodiment 2 |
|---|---|---|
| Electrode material | Graphene | Platinum |

Figure 10:
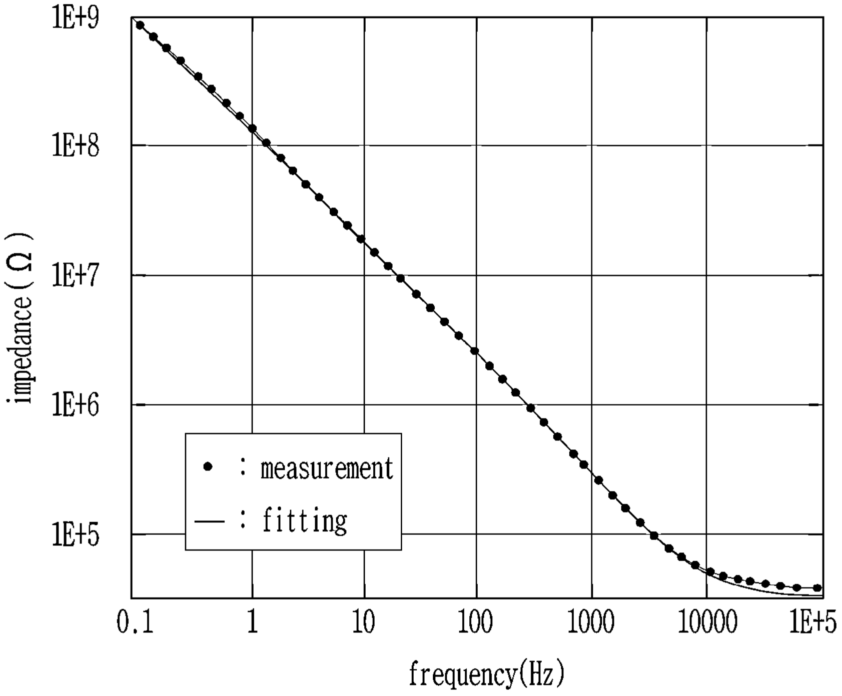
FIG. 10 is a graph illustrating impedance of the electrode sites according to Comparative Example 5.
Figure 11:
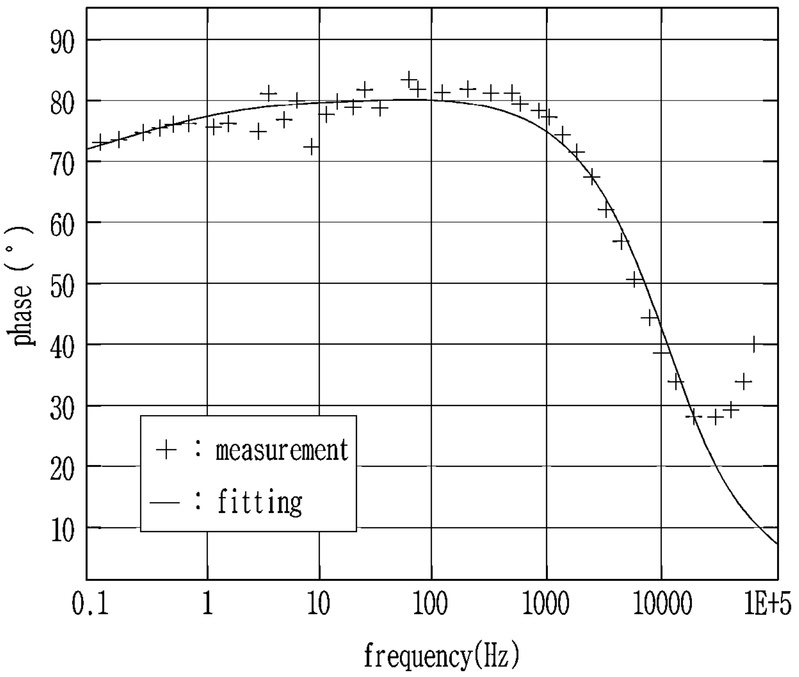
FIG. 11 is a graph illustrating phases of the electrode sites according to Comparative Example 5.
Figure 12:
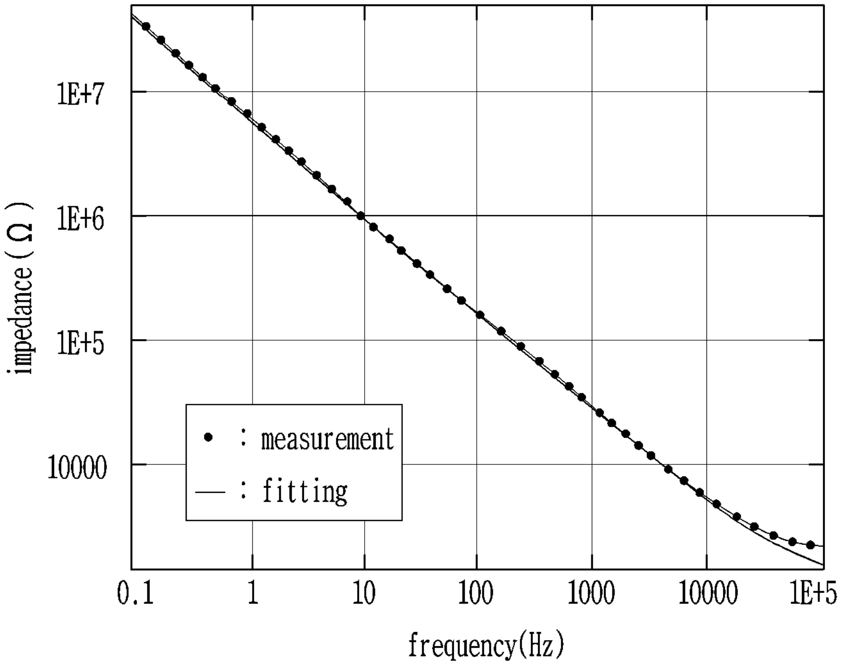
FIG. 12 is a graph illustrating impedance of the electrode sites according to Exemplary Embodiment 2.
Figure 13:
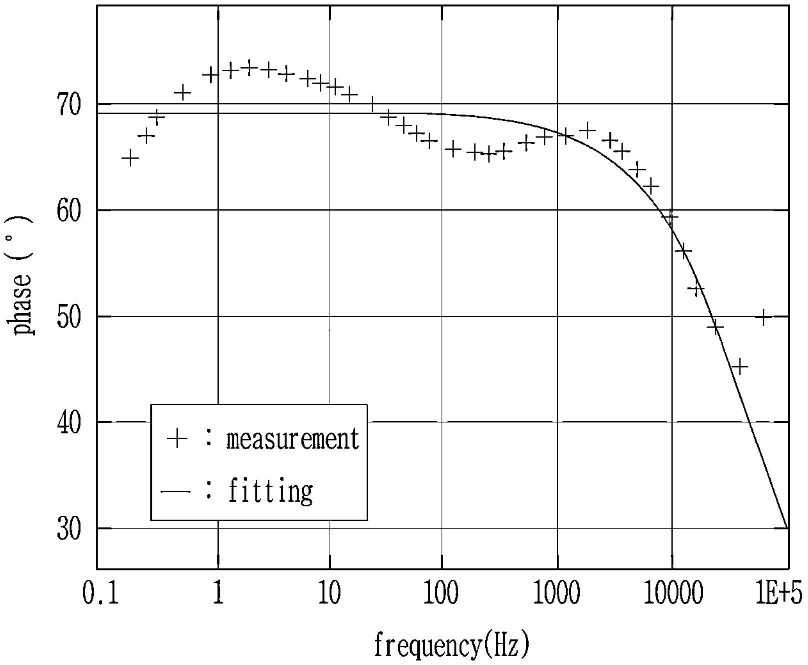
FIG. 13 is a graph illustrating phases of the electrode sites according to Exemplary Embodiment 2.

FIG. 10 is a graph illustrating the impedance (Ω) of Comparative Example 5, FIG. 11 is a graph illustrating the phases (°) of Comparative Example 5, FIG. 12 is a graph illustrating the impedance (Ω) of Exemplary Embodiment 2, and FIG. 13 is a graph illustrating the phases (°) of Exemplary Embodiment 2. Considering that fitting is good when the impedance and phase measurement results are electrically modeled, it is confirmed that both electrodes are properly modeled. When the two electrodes are compared with each other, it is confirmed that the platinum electrode (Exemplary Embodiment 2, in FIG. 12) has the impedance of several tens of kiloohms (kΩ) at a frequency of 1 kHz, whereas the graphene electrode (Comparative Example 5, in FIG. 10) has the impedance of several hundreds of kiloohms at the same frequency. Considering the impedance of the platinum electrode is about 10 times lower than that of graphene, it may be confirmed that the allowable amount of current is about 10 times higher. Whereas, the graphene electrode has an advantage in that the graphene electrode is transparent even though the allowable current thereof is about 10 times lower than that of platinum.

In the present disclosure, it may be predicted that two advantages of transparency and electrical conductivity may be evenly provided by arranging two materials in appropriate regions (i.e. the metal material is placed on the electrode sites, and the carbon material is placed on the interconnector).

Although the exemplary embodiments of the present disclosure have been described in detail above, the scope of the present disclosure is not limited thereto, and various modifications and improvements of those skilled in the art using the basic concepts of the present disclosure as defined in the following claims are also included in the scope of the present disclosure.

DESCRIPTION OF THE REFERENCE NUMERALS IN THE DRAWINGS

100: deep brain stimulation transparent electrode array
110: substrate 120: electrode sites
121: graphene sheet 130: electrically conductive contacts
140: interconnector 141: electrode site electrical signal transmission circuit
142: contact electrical signal transmission circuit 150: overlayer
151, 152: openings
200: optical fiber
201: core 202: adhesive layer
203: cladding

INDUSTRIAL APPLICABILITY

By using the deep brain stimulation transparent electrode array, which is transparent and has low-interference, and the neural signal detection method using the same according to the present disclosure, a new research tool may be provided to brain and neuroscience researchers as well as patients and hospitals, which are associated with neurological disorders. In addition, the present disclosure is applicable to various body parts such as the spine, joints, and muscles, so as to be applicable to research on an optic nerve test sensor, a diabetes measurement sensor, a neurotransmitter sensor, and the like in the future.

The invention claimed is:

1. A deep brain stimulation transparent electrode array comprising:

an optically transparent biocompatible dielectric substrate;

a plurality of electrode sites disposed on one side of the biocompatible dielectric substrate;

a plurality of electrically conductive contacts disposed on another side of the biocompatible dielectric substrate;

an interconnector extending from the plurality of electrode sites and connecting the plurality of electrically conductive contacts and the plurality of electrode; and an optical fiber bonded to an underside of the biocompatible dielectric substrate and configured to deliver optical stimulation and perform optical sensing, wherein each of the plurality of electrode sites is made of a metal material, and the interconnector is made of a carbon material in a form of one to ten layers of graphene sheets, and wherein a length of one end of the biocompatible dielectric substrate is longer than a length of one end of the optical fiber, and the one end of the biocompatible dielectric substrate is folded toward the one end of the optical fiber, so that a part or all of each of the plurality of electrode sites covers the one end of the optical fiber and so that light is configured to pass around the electrode sites and through the substrate to and/or from the optical fiber.

2. The deep brain stimulation transparent electrode array of claim 1, wherein the metal material is at least one selected from a group consisting of platinum, iridium, tungsten, iron, nickel, copper, zinc, titanium, aluminum, silver, gold, and alloys thereof.

3. The deep brain stimulation transparent electrode array of claim 1, wherein respective junction parts between the plurality of electrode sites and the interconnector are subjected to thermal annealing or current annealing.

4. The deep brain stimulation transparent electrode array of claim 1, wherein the biocompatible dielectric substrate is disposed to surround the optical fiber.

5. The deep brain stimulation transparent electrode array of claim 1, wherein the biocompatible dielectric substrate and the optical fiber are bonded to each other by at least one adhesive selected from a group consisting of polydimethylsiloxane, polyimide, and silylated polyurethanes.

6. A method of detecting neural signals using the deep brain stimulation transparent electrode array according to claim 1, comprising:

inserting the deep brain stimulation transparent electrode array onto electrically active biological tissue; and recording neural responses generated by nerve cells in nerve tissue at each of the plurality of electrode sites.

* * * * *